United States Patent
Arnold

(10) Patent No.: US 10,792,259 B2
(45) Date of Patent: Oct. 6, 2020

(54) COMPOSITIONS COMPRISING BETA-HYDROXYBUTYRIC ACID AND SALT, AND METHODS OF USING THE SAME

(71) Applicant: SavInd, Inc., Urbana, IL (US)

(72) Inventor: Patrick Arnold, Champaign, IL (US)

(73) Assignee: SavInd, Inc., Urbana, IL (US)

( * ) Notice: Subject to any disclaimer, the term of this patent is extended or adjusted under 35 U.S.C. 154(b) by 0 days.

(21) Appl. No.: 16/817,040

(22) Filed: Mar. 12, 2020

(65) Prior Publication Data

US 2020/0206168 A1 Jul. 2, 2020

Related U.S. Application Data

(63) Continuation of application No. 15/470,179, filed on Mar. 27, 2017, now Pat. No. 10,588,877.

(60) Provisional application No. 62/365,156, filed on Jul. 21, 2016.

(51) Int. Cl.
*A61K 31/191* (2006.01)
*A61K 9/08* (2006.01)
*A61K 9/48* (2006.01)

(52) U.S. Cl.
CPC .............. *A61K 31/191* (2013.01); *A61K 9/08* (2013.01); *A61K 9/48* (2013.01)

(58) Field of Classification Search
CPC ........... A61K 31/191; A61K 9/08; A61K 9/48
See application file for complete search history.

(56) References Cited

U.S. PATENT DOCUMENTS

| 5,292,774 | A | 3/1994 | Hiraide et al. |
| 5,461,073 | A | 10/1995 | Katayama |
| 8,541,468 | B2 | 9/2013 | Umeda et al. |
| 9,138,420 | B2 | 9/2015 | D'Agostino et al. |
| 9,273,331 | B2 | 3/2016 | Kawata |
| 2006/0280721 | A1 | 12/2006 | Veech et al. |
| 2012/0053240 | A1 | 3/2012 | Rathmacher et al. |

OTHER PUBLICATIONS

Bough, K., et al. (2007) "Anticonvulsant Mechanisms of the Ketogenic Diet", Epilepsia 48:1, 43-58.
Fioretto, P., et al. (1987) "Glomerular Filtration Rate is Increased in Man by the Infusion of Both D, L-3-Hydroxybutyric Acid and Sodium D, L-3-Hydroxybutyrate*" Journal of Clinical Endocrinology and Metabolism, 65:2, 331-338.
Yamada, K., et al., (1993) "Enzymatic degradation of poly(hydroxyalkanoates) by Pseudomonas pickettii" Int. J. Biol. Macromol, 15: 215-220.
Product Label for KetoSports KetoForce (Apr. 8, 2016). Can be accessed at https://www.amazon.com/KetoSports-KetoForce-Original-Exogenous-Product/dp/B00U7R6Z1E/ref=sr_1_1_a_it?s=instant-video&ie=UTF8&qid=1488920029&sr=8-1&keywords=ketosports+ketoforce.
Office Action (Final) from corresponding U.S. Appl. No. 15/470,179, dated Jul. 19, 2018.
Office Action (Non-Final) from corresponding U.S. Appl. No. 15/470,179, dated Feb. 1, 2018.

*Primary Examiner* — Zohreh A Fay
(74) *Attorney, Agent, or Firm* — Harness, Dickey & Pierce, PLC

(57) ABSTRACT

β-hydroxy butyric acid in combination with β-hydroxybutyrate salts are useful to induce ketosis, achieving blood ketone levels of (0.5-6.0 mmol/L), with or without dietary restriction, and without inducing harmfully high mineral loads in the blood. The combination of β-hydroxy butyric acid and salt results in substantial improvements in metabolic bookmakers related to insulin resistance, diabetes, weight loss, and physical performance & endurance in a short period of time. Further, use of these supplements to achieve ketosis yields a significant elevation of blood ketones and reduction of blood glucose levels. These acid/salt mixtures are also useful for suppressing appetite, preventing epileptic seizures, and treating cancer.

17 Claims, 1 Drawing Sheet

COMPOSITIONS COMPRISING BETA-HYDROXYBUTYRIC ACID AND SALT, AND METHODS OF USING THE SAME

CROSS-REFERENCE TO RELATED APPLICATIONS

This application is a continuation application of U.S. patent application Ser. No. 15/470,179, filed Mar. 27, 2017, now U.S. Pat. No. 10,588,877, issued Mar. 17, 2020, which claims the benefit and priority to U.S. Provisional Patent Application No. 62/365,156, filed on Jul. 21, 2016. The entire disclosures of the applications identified in this paragraph are incorporated herein by references.

FIELD

The present disclosure relates to compositions of β-hydroxy butyric acid and β-hydroxybutyrate salts. Such compositions are useful for inducing ketosis in subjects in need thereof. Methods of making these compositions are also disclosed herein, along with methods of using the compositions in circumstances in which ketosis is useful or salutary.

BACKGROUND

Ketones can serve as energy substrates—in place of glucose—for both peripheral tissues and the central nervous system. The two most abundant and physiologically significant ketone bodies are acetoacetates and β-hydroxybutyrate (βHB). A third ketone body, acetone, is produced as a byproduct that is exhaled from the lungs. The body produces ketone bodies during nutritional or therapeutic ketosis in the range of 0.5-6.0 mmol/L. Elevated blood ketone concentrations (i.e., "ketosis") are associated with anticonvulsant effects, enhanced brain metabolism, neuroprotection, muscle sparing properties, and improvement in cognitive and physical performance. Most methods of inducing ketosis involve ketogenic diets, caloric restriction, therapeutic fasting, and/or supplementation with ketogenic precursors.

KetoForce® is a βHB product, comprising a ~50% blend of potassium and sodium salts in a 50% w/v solution. KetoForce® has a pH adjusted to around 10.5. While KetoForce® can be consumed by itself, it can also be mixed with other ketogenic ingredients.

U.S. Pat. No. 9,138,420 to D'Agostino reports that ketosis can be induced by administration of compositions comprising βHB mineral salts in combination with medium chain fatty acids. D'Agostino also asserts that buffering β-hydroxy butyric acid with Na-βHB causes harmful sodium overload and is ineffective to prevent seizures in animal models.

U.S. Pat. No. 5,292,774 to Hiraide reports a substitution fluid containing at least one of containing at least one βHB selected from 3-hydroxy butyric acid, 3-sodium hydroxybutyrate, and 3-potassium hydroxybutyrate. These substitution fluid mixes are useful for sustaining patients who are having difficulty metabolizing carbohydrates. Because Hirade does not disclose any actual mixtures of free acid and salt, Hirade also does not disclose any particular ratios in which βHB free acid and salt are to be mixed.

Fioretto et al. (1987) *J. Clin. Endocrinol. & Metab.* 65:331-38 report administering infusions of either β-hydroxy butyric acid or Na-βHB to improve kidney functions in diabetic patients. Fioretto, however, does not report mixtures of free acid and sodium salts.

SUMMARY

Although it has been believed in the art that mixtures of β-hydroxy butyric acid and βHB salts can cause harmful mineral overload (see, D'Agostino supra), the present inventors have discovered that when β-hydroxy butyric acid and βHB salts are combined in particular ratios, the resulting composition is not only not harmful, it is actually safer and more effective for inducing ketosis. The present disclosure provides compositions comprising β-hydroxy butyric acid and βHB salts at a ratio between ~125 parts free acid per ~7 parts salt to ~0.4 parts free acid per ~125.1 parts salt. The present disclosure also discloses method to elevate and sustain blood ketone body levels through the administration of these compositions.

In certain embodiments, the induced ketosis can suppress appetite. In certain embodiments, the induced ketosis can enhance weight loss. In certain embodiments, the induced ketosis can increase athletic endurance. In certain embodiments, the induced ketosis can control blood sugar concentrations. In certain embodiments, the induced ketosis can be used to treat epilepsy, cancer, and/or diabetes.

Other embodiments, including particular aspects of the embodiments summarized above, will be evident from the detailed description that follows.

DETAILED DESCRIPTION

Figure 1A:
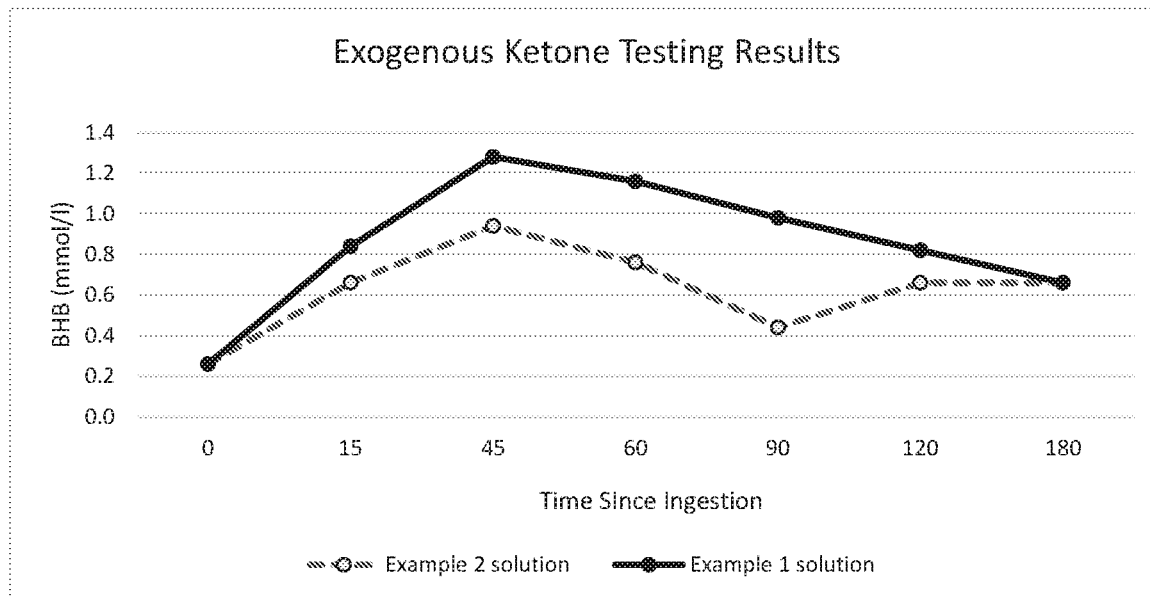
FIG. 1A shows blood ketone concentration and FIG. 1B shows blood glucose concentration following administration of βHB supplement.

Glossary. As used herein, "β-hydroxy butyric acid" refers to the free acid form of 3-hydroxybutanoic acid. By contrast, "β-hydroxybutyrate"—or "βHB" for short refers to a salt form of the β-hydroxy butyric acid. Unless otherwise specified, all ratios given herein are mass:mass ratios. "Keto sis" is the physiological state of elevated blood ketone body levels (typically >0.5 mmol/L). "Keto sis" should not be confused with "ketoacidosis," which is the runaway accumulation of ketone bodies (typically >25 mmol/L) in the blood, and associated drop in blood pH.

Concentrations, amounts, solubilities, and other numerical data may be expressed or presented herein in a range format. It is to be understood that such a range format is used merely for convenience and brevity, and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "~1 to ~5" should be interpreted to include not only the explicitly recited values of ~1 to ~5, but also include the individual values and sub-ranges within the indicated range. Thus, included in this numerical range are individual values such as 1, 2, 3, 4, & 5. Sub-ranges such as 1-3, 2-4, and 3-5, etc. are also included. This same principle applies to ranges reciting only one numerical value. Furthermore, such an interpretation should apply regardless of the range or the characteristics being described. As used herein, a tilde in front of a number signifies "approximately" (e.g., ~2=approximately 2).

As used herein "w/v %" conveys grams of a dissolved substance with a total volume of 100 mL. For example, 12 grams of sucrose in aqueous solution of total volume one liter would be a 1.2% (w/v) sucrose solution (12 g in 1000 mL=1.2 g in 100 mL).

As used herein "patient," means members of the animal kingdom, including mammals, such as but not limited to, primates including humans, gorillas and monkeys; rodents, such as mice; fish; reptiles; and birds. The patient may be any animal requiring therapy, treatment, or prophylaxis, or any animal suspected of requiring therapy, treatment, or prophylaxis. "Patient" and "subject" are used interchangeably herein. As used in this definition only, "treatment" means that the regimen described is continued until the underlying disease is resolved, whereas "therapy" requires only that the regimen alleviate one or more symptoms of the underlying disease. "Prophylaxis" means that regimen is undertaken to prevent a possible occurrence, such as where a high glucose or diabetes is identified.

"Keto-adaptation" refers to prolonged nutritional ketosis (>1 week) to achieve a sustained nonpathological "mild ketosis" or "therapeutic ketosis."

"A, B, and/or C" conveys the set composed of A, B, C, A&B, A&C, B&C, and A&B&C, "Or" conveys the inclusive alternative conjunction.

All documents referenced herein are hereby incorporated by reference in their entireties, except that where a document incorporated by reference defines a term in a manner not identical to the way that the term is defined in the present disclosure, the definition provided in the present disclosure controls.

Compositions. Compositions of ketone precursors are disclosed herein, which comprise β-hydroxy butyric acid and βHB in a ratio ranging from ~125 parts free acid per ~7 parts salt to ~0.4 parts free acid per ~125.1 parts salt. In certain embodiments, the free acid may be combined with the salt or salts in ratios ranging from ~125 parts free acid per ~7 parts salt to ~75 parts free acid per ~57.5 parts salt. In certain embodiments, the free acid may be combined with the salt or salts in ratios ranging from ~75 parts free acid per ~57.5 parts salt to ~0.4 parts free acid per ~125.1 parts salt. In certain embodiments, the free acid may be combined with the salt or salts in ratios ranging from ~75 parts free acid per ~57.5 parts salt to ~38.5 parts free acid per ~90 parts salt. In certain embodiments, the free acid may be combined with the salt or salts in ratios ranging from ~102 parts free acid per ~30 parts salt to ~75 parts free acid per ~57.5 parts salt. In certain embodiments, the free acid may be combined with the salt or salts in ratios ranging from ~102 parts free acid per ~30 parts salt to ~38.5 parts free acid per ~90 parts salt. In certain embodiments, the free acid may be combined with the salt or salts in ratios ranging from ~80.8 parts free acid per ~50 parts salt to ~60 parts free acid per ~70 parts salt. In certain embodiments, the number of weight parts of βHB free acid per weight parts of βHB salts can be calculated as a function of the weight parts of salt in the mixture, according to the equation $y=-1.0577x+133.65$, where "y" represents weight parts of free acid and "x" represents weight parts of salt.

In certain embodiments, the composition comprises a mix of free acid, sodium salt, and potassium salt. For example, the composition can comprise a mass:mass:mass ratio of ~125 parts free acid per ~3.7 parts potassium salt per ~3.3 parts sodium salt to ~0.4 parts free acid per ~66.3 parts potassium salt per ~58.8 parts sodium salt. At ~125:3.7 K:3.3 Na, the overall composition will have a pH~3.2 in 50% (w/v) aqueous solution. At 125:4:66.3 K:5.8 Na, the overall composition will have a pH~8.0 in 50% (w/v) aqueous solution. In certain embodiments, the composition will have a PH~4.5 and will comprise ~75 parts free acid per ~30.5 parts potassium salt per ~27 parts sodium salt. In certain embodiments, the composition comprises a mix of free acid, magnesium salt, and calcium salt. In certain embodiments, the composition comprises a mix of free acid, histidine salt, and sodium salt. In certain embodiments, the composition comprises a mix of free acid, histidine salt, and potassium salt. In certain embodiments, the composition can be assembled by mixing 2.9 volume parts of a 50% (w/v) aqueous solution of β-hydroxybutyric acid with 2.5 volume parts of KetoForce® (e.g., KetoForce® as was being distributed in July 2016) in 50% (w/v) aqueous solution to achieve a solution with pH~4.5. Such a solution has a pH suitable for shelf-stability in a form that includes appropriate sweetener and flavoring agents necessary to achieve a drink that is acceptably palatable.

The person of ordinary skill will appreciate that the ratio of free acid to salt will determine the pH of the composition. In certain embodiments, the composition will have a pH from ~3.2 to ~8.5 in a 50% (w/v) aqueous solution, for example from ~3.2 to ~8, or from ~3.2 to ~4.5, or from ~4 to ~8, or from ~4 to ~6, or from ~4 to ~5. In certain embodiments, the composition will have a pH~4.5. The person of ordinary skill will also appreciate that the pH affects both the shelf stability and the flavor of the composition.

Nonlimiting examples of the salts that may be used include calcium βHB, lithium βHB, magnesium βHB, potassium βHB, sodium βHB, agmatine βHB, arginine βHB, citrulline βHB, creatine βHB, histidine βHB, lysine βHB, ornithine βHB, and combinations thereof. Nonlimiting examples of salt combinations include sodium and arginine salts or sodium and potassium salts. Other non-limiting examples of β-hydroxybutyrate ketone sources include 1,3-butanediol, ethyl acetoacetates, and ethyl β-hydroxybutyrate.

In certain embodiments, the compositions are optionally administered at doses between about 2 grams and about 50 grams, for example between about 5 grams and about 30 grams, or between about 10 grams and about 20 grams. For example, the ketone compositions are optionally administered at doses of about 2 grams, about 4 grams, about 5 grams, about 6 grams, about 7 grams, about 8 grams, about 9 grams, about 10 grams, about 11 grams, about 12 grams, about 13 grams, about 14 grams, about 15 grams, about 17 grams, about 19 grams, about 20 grams, about 22 grams, about 24 grams, about 26 grams, about 28 grams, about 30 grams, about 32 grams, about 34 grams, about 36 grams, about 38 grams, about 40 grams, about 42 grams, about 44 grams, about 46 grams, about 48 grams, or about 50 grams. The frequency of administration of the agent can vary depending on any of a variety of factors, such as timing of treatment from previous treatments, objectives of the treatment (e.g., weight loss or treatment of cancer or neurological disease), and the like. The duration of administration of the agent, i.e., the period of time over which the agent is administered, can vary, depending on any of a variety of factors, including patient response, desired effect of treatment, etc. Dosage amount can vary according to factors such as the degree of susceptibility of the individual, the age, sex, and weight of the individual, idiosyncratic responses of the individual, the dosimetry, and the like. Optimization of such factors is routine in the art.

The amount of the compositions described herein to be administered will depend on absorption, distribution, metabolism, and excretion rates of the βHB salts in combination with the free acid and the various catabolic products, the method of administration, and the particular disorder being treated, as well as other factors known to those of skill in the art. The dose should be sufficient to effect a desirable response, such as a therapeutic or prophylactic response against a particular disorder or condition, taking into account the severity of the condition to be alleviated. The compositions may be administered once, or may be divided and administered over intervals of time. It is to be understood that administration may be adjusted according to individual need and professional judgment of a person administrating or supervising the administration of the compositions described herein.

In certain embodiments, the βHB compound is histidine βHB, ornithine βHB, creatine βHB, agmatine βHB, or citrulline βHB. In certain embodiments, the β-hydroxy butyric acid or salt is a racemic mixture of D- and L-β-hydroxy butyric acid or salt. In certain embodiments the β-hydroxy butyric acid or salt is a single isomer D-β-hydroxy butyric acid or salt. D-β-hydroxy butyric acid is a powder at room temperature while racemic β-hydroxy butyric is a liquid. In certain embodiments where the composition is provided as a dry powder, the composition may be assembled by mixing a racemic mixture of the free acid with a salt or set of salts that are enriched or purified for the D isomer. In other dry powder embodiments, the composition may be assembled by mixing a free acid that has been enriched or purified for the D isomer with a racemic mixture of salt or salts. In certain dry power embodiments, the composition may be assembled using stocks of both free acid and salt or salts that have been enriched or purified for the D isomer. In certain embodiments, D-β-hydroxy butyric acid powder is mixed with D-β-hydroxybutyrate salt powders. In certain embodiments, racemic β-hydroxy butyric acid liquid is mixed with racemic β-hydroxybutyrate salt powders, and a solution thereof is dried onto a solid substrate carrier (e.g., maltodextrin or dry milk solids). In certain embodiments, racemic β-hydroxy butyric acid liquid is mixed with D-β-hydroxybutyrate salts, and a solution thereof is dried onto a solid substrate carrier.

In certain embodiments, the compositions described herein may further comprise one or more additional ketone precursors or supplements in combination with βHB, including but not limited to acetoacetates, ketone esters, and other compounds that cause a rise in blood ketone levels. In certain embodiments, the compositions described herein may further comprise medium chain triglycerides. Details concerning appropriate triglycerides can be found in U.S. Pat. No. 9,138,420 (particularly column 7). The entire contents of U.S. Pat. No. 9,138,420 are herein incorporated by reference.

In certain embodiments, the compositions described herein may include one or more βHB mineral salts, including but not limited to potassium, sodium, calcium, magnesium, and lithium salts of βHB, and combinations thereof, as well as any other feasible non-toxic mineral salts of βHB. Organic salts of βHB include, without limitation arginine, lysine, histidine, ornithine, creatine, agmatine, and citrulline βHB. The salts may contain the racemic D/L-βHB or the single D isomer.

Composition described herein may also optionally include at least one non-toxic mineral salt. Non-limiting examples include Co, Cr, Cu, K, Mg, Mn, Mo, Na, Se, V, and Zn associated with an ion of chlorine, sulfate, iodine, bromine, or other known ion in the art. For example, the mineral salt can be selected from sodium chloride, zinc sulfide, and potassium iodine.

In certain embodiments, the composition described herein may also include one or more nutritional substrates such as free amino acids, amino acid metabolites, vitamins, minerals, electrolytes and metabolic optimizers such as NADH, soluble ubiquinol, tetrahydrobiopeterin, α-ketoglutaric acid, carnitine, and/or α lipoic acid, nutritional co-factors, calcium β-methyl-β-hydroxybutyrate, arginine α-ketoglutarate, sodium R-α lipoic acid, thiamine, riboflavin, niacin, pyridoxine, ascorbic acid, citric acid, malic acid, sodium benzoate, potassium sorbate, acesulfame K, aspartame, xanthan gum, or a combination thereof. Nonlimiting examples of nutritional co-factors include R-α lipoic acid, acetyl-1-carnitine, ketoisocaproate, α-ketoglutarate, α-hydroxyisocaproate, creatine, branched chain amino acids (leucine, isoleucine, valine), β-hydroxy-β-methylbutyrate (HMB), B vitamins, vitamin C, soluble ubiquinol, and carnitine to assist in mitochondrial function. In certain embodiments, the composition is dosed to provide no more than 400 calories per day.

Methods of use. The compositions described herein are useful for many purposes. For example, in certain embodiments these compositions can be consumed by those who wish to reduce body mass to suppress appetite and to accelerate and facilitate weight loss.

In certain embodiments, these compositions can be consumed by diabetics and those diagnosed as pre-diabetic to control blood glucose and/or to ameliorate type II diabetes. In certain embodiments, a patient's blood glucose concentrations are at least 5%, for example at least 10%, at least 20%, at least 30%, at least 40%, at least 45%, or even at least 50% lower within a week after having begun consuming the compositions described herein, relative to the same patient's blood glucose immediately prior to commencement of the course of composition administration. In certain embodiments, variation among individual blood glucose readings from a single patient will decrease by at least 5%, for example at least 10%, at least 20%, at least 30%, at least 40%, at least 45%, or even at least 50% within a week after having begun consuming the compositions described herein, relative to the variation among individual readings of the same patient's blood glucose during the week immediately prior to commencement of the course of composition administration.

In certain embodiments, these compositions can be consumed by epileptics and those diagnosed as prone to seizures to control and/or to ameliorate incidence of seizures.

In certain embodiments, these compositions can be consumed by cancer patients and those recently cured from cancer to suppress tumor growth and ameliorate disease.

In certain embodiments, these compositions can be consumed by an athlete to enhance athletic performance, to improve endurance, and/or as an adjunct to a ketogenic diet.

In certain embodiments, these compositions may be consumed to prevent diseases related to metabolic dysfunction, to prevent diseases related to mitochondrial defect, to prevent insulin resistance, as an anti-aging supplement, and for other uses concerning improved metabolic health.

In certain embodiments, the composition may be consumed as a solution, for example a 50% (w/v) aqueous solution. In certain embodiments, the composition may be consumed as a suspension or an emulsion. Additionally or alternatively, the composition may be consumed as a dry powder. When the composition is consumed in dry powder form, the composition may optionally be formulated in a tablet, a capsule, a sachet, and/or any other pharmaceutically acceptable dry dosage form known in the art, including a concentrated gel. In certain embodiments, these compositions can be delivered in the form of a ready-to-drink formulations, optionally including coconut milk powder. The drink may be pH adjusted with citric and/or malic acid, and artificial sweetener or flavoring can be added. The drink can be homogenized and/or pasteurized.

In certain embodiments, the user also follows a ketogenic diet that restricts intake of carbohydrates and protein during the period of administration of the composition as described herein. In specific embodiments, the patient restricts the dietary intake to a caloric ratio of about 70% fat, 25% protein, and 5% carbohydrates. The therapeutic ketosis produced herein provides a rapid and sustained keto-adaptation as a metabolic therapy for a wide range of metabolic disorders, and provides nutritional support for therapeutic fasting, weight loss, and performance enhancement. As such, the composition as described herein is optionally administered once per day, twice per day, or three times per day to a subject desiring to promote and/or sustain a state of ketosis.

Although oral administration dosage forms are described above, such disclosures should not be construed to limit scope of the present description. Other routes of administration are also contemplated by the present disclosure, such as but not limited to intragastric and parenteral (referring to intravenous and intra-arterial and other appropriate parenteral routes) administration.

Because the compositions and methods described herein raise blood ketone concentration, the subject may enjoy greater flexibility in the diet that must be followed to maintain a state of ketosis. Thus, while consistently taking the compositions described herein, a subject may be able to enjoy an occasional carbohydrate "cheat" without ablating the ketogenic state. Indeed, because the formulations disclosed herein facilitate quick and easy transition into ketosis, should one need to depart from a strict ketogenic diet for a limited time, getting back into ketosis can be accomplished quickly and without the difficult symptoms which heretofore impeded the process.

Through the consumption of the compositions described herein, a measureable increase in blood ketones can often be observed within hours of taking the compositions. This is particularly true if the subject maintains a ketogenic diet while taking the compositions. Thus, whereas it may take weeks to measure an increase of blood ketones following a ketogenic diet alone, the utilization of the compositions described herein will allow the increase of blood ketones to be measured quickly, thereby encouraging and motivating those pursuing a state of ketosis.

In the following examples, reference is made to the accompanying drawings, which form a part hereof, and within which are shown by way of illustration specific embodiments of the compositions and methods disclosed and described herein. It is to be understood that other embodiments may be utilized and structural changes may be made without departing from the scope of the invention.

EXAMPLES

Example 1

Solution of DITB Acid with Sodium and Potassium Hydroxide

Without being bound by theory, the inventors of the compositions and methods disclosed herein hypothesized that osmotic effects may stimulate peristalsis and quick emptying of the bowels, thus limiting the ability of the body to absorb βHB from prior art βHB salt solutions. It has not previously been appreciated in the art that osmotic effects from mineral salts could be limiting ketone absorption. However, it is known in the art that excessive quantities of βHB free acid can be toxic, which is why prior art ketogenic formulations make use of βHB salts. Therefore, the inventors experimented with solutions that have reduced mineral salt content to achieve enhanced ketone absorption. One such solution having reduced mineral salt content was made by diluting 23.1 kg β-hydroxy butyric acid in water to 50% concentration (w/v) in a vessel containing a stirrer and a cooling jacket. 13.6 kg of KOH and 1.61 kg of NaOH were slowly added while coolant was circulated through the jacket. Alkali was added in a controlled manner, such that the solution temperature was never permitted to exceed 60° C.

After all ingredients were added, the solution was diluted to 592 liters and allowed to cool to room temperature. The aqueous solution contained (w v) 43.7% β-hydroxybutyrate, 3.1% potassium, and 3.2% sodium. The final pH was 4.4.

Example 2

Solution of Sodium and Potassium βHB 47 kg of sodium β-hydroxybutyrate and 53 kg of potassium β-hydoxybutyrate (previously dried in a dessicator over phosphorous pentoxide) were dissolved in water to a final volume of 200 liters. The final aqueous solution had a pH of 10.5 and contained (w/v) 39% β-hydroxybutyrate, 5.5% sodium, and 5.5% potassium.

Example 3

Human Trials

Seven participants (three women, four men) ranging in age from 32 to 60 years old were administered 30 mL of the solution of Example 1, containing 11.7 g β-hydroxybutyrate, 819 mg potassium, and 837 mg sodium. The solution was diluted to 480 mL and consumed after an overnight fast. On a separate occasion, the same seven participants were administered 30 mL of the solution of Example 2, containing 11.7 g β-hydroxybutyrate, 1.6 g potassium, and 1.6 g sodium. Just as with the trial of the Example 1 solution, the Example 2 solution was diluted to 480 mL and consumed after an overnight fast.

Figure 1B:
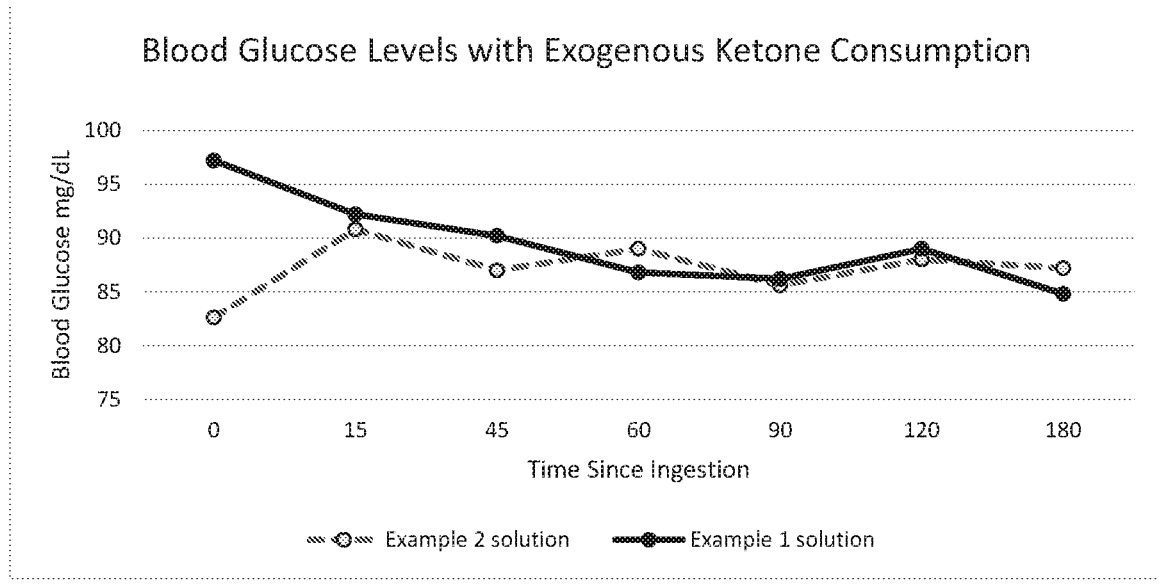

Levels of β-hydroxybutyrate and glucose in the blood were measured during each trial using a PRECISION XTRA ketone/glucose blood monitoring device (Abbot Labs, Chicago, Ill.). Readings were taken immediately before administration of the solution and then at 15, 45, 60, 90, 120, & 180 minutes post-administration. Blood ketone levels are shown in FIG. 1A. Blood glucose levels are shown in FIG. 1B. The results of these trials are also summarized in Table 1 below.

TABLE 1

| Blood component concentrations post-administration of solution | | | | | | | |
|---|---|---|---|---|---|---|---|
| Time (min.) | 0 | 15 | 45 | 60 | 90 | 120 | 180 |
| βHB (mmol/L) | | | | | | | |
| Example 1 solution | 0.3 | 0.8 | 1.3 | 1.2 | 1.0 | 0.8 | 0.7 |
| Example 2 solution | 0.3 | 0.7 | 0.9 | 0.8 | 0.4 | 0.7 | 0.7 |
| Glucose (mg/dL) | | | | | | | |

TABLE 1-continued

Blood component concentrations post-administration of solution

| Time (min.) | 0 | 15 | 45 | 60 | 90 | 120 | 180 |
|---|---|---|---|---|---|---|---|
| Example 1 solution | 97.2 | 92.2 | 90.2 | 86.8 | 86.2 | 89 | 84.8 |
| Example 2 solution | 82.6 | 90.8 | 87 | 89 | 85.6 | 88 | 87.2 |

It is known in the art that βHB salt solutions can have mild adverse gastro-intestinal ("GI") effects, including upset stomach and diarrhea. It was also unexpectedly found that fewer subjects reported adverse GI effects following administration of Example 1 solution than following administration of Example 2 solution.

In the preceding specification, all documents, acts, or information disclosed do not constitute an admission that the document, act, or information of any combination thereof was publicly available, known to the public, part of the general knowledge in the art, or was known to be relevant to solve any problem at the time of priority unless otherwise stated. The preceding examples are merely illustrative, and should not be read to limit the scope of the invention as defined by the following claims.

What is claimed is:

1. A composition comprising β-hydroxybutyric free acid and β-hydroxybutyrate salt, wherein the free acid and salt stand in a mass:mass ratio from about 75 parts free acid:about 57.5 parts salt to about 38.5 parts free acid:about 90 parts salt, wherein the salt is a mixture of potassium and sodium salts.

2. The composition of claim 1, wherein the pH of the composition is about 3.2 to about 8.0 in a 50% (w/v) aqueous solution.

3. The composition of claim 2, wherein the pH of the composition is about 4.0 to about 6.0.

4. The composition of claim 3, wherein the pH of the composition is about 4.0 to about 5.0.

5. The composition of claim 4, wherein the pH of the composition is about 4.5.

6. The composition of claim 2, wherein the salt further comprises calcium, magnesium, or a combination thereof.

7. The composition of claim 1, wherein the composition comprises both D and L isomers of β-hydroxybutyric free acid and/or β-hydroxybutyrate salt.

8. The composition of claim 7, wherein the β-hydroxybutyric free acid and/or β-hydroxybutyrate salt is/are present as a racemic mixture.

9. The composition of claim 1, wherein the composition is a dry powder.

10. The composition of claim 9, wherein β-hydroxybutyric free acid and β-hydroxybutyrate salt are each present as D isomer.

11. The composition of claim 1, wherein the free acid and salt stand in a mass:mass:mass ratio from ~125 parts free acid:~3.7 parts potassium salt:~3.3 parts sodium salt to ~0.4 parts free acid:~66.3 parts potassium salt:~58.8 parts sodium salt.

12. The composition of claim 11, wherein the mass:mass:mass ratio is about 43 parts free acid:about 23 parts potassium salt:about 35 parts sodium salt.

13. A pharmaceutical dosage form comprising the dry powder of claim 9, wherein the pharmaceutical dosage form is a table or a capsule.

14. A method of inducing ketosis in an individual in need thereof, the method comprising administering to the individual an aqueous solution of the composition of claim 1.

15. The method of claim 14, wherein the pH of the composition is about 3.2 to about 8.0 in a ~50% (w/v) aqueous solution.

16. The method of claim 15, wherein the pH is about 4.5.

17. The method of claim 14, wherein the free acid and salt stand in a mass:mass:mass ratio from ~125 parts free acid:~3.7 parts potassium salt:~3.3 parts sodium salt to ~0.4 parts free acid:~66.3 parts potassium salt:~58.8 parts sodium salt.

* * * * *